United States Patent [19]

Spitler

[11] Patent Number: 4,489,710

[45] Date of Patent: Dec. 25, 1984

[54] COMPOSITION AND METHOD FOR TRANSPLANTATION THERAPY

[75] Inventor: Lynn E. Spitler, Tiburon, Calif.

[73] Assignee: Xoma Corporation, San Francisco, Calif.

[21] Appl. No.: 434,782

[22] Filed: Oct. 18, 1982

Related U.S. Application Data

[62] Division of Ser. No. 276,579, Jun. 23, 1981, abandoned.

[51] Int. Cl.[3] .................... C07G 17/00; C07G 7/00; C07G 11/00; A61K 39/00

[52] U.S. Cl. .................... 128/1 R; 424/85

[58] Field of Search .................... 424/85; 128/1 R; 435/1

[56] References Cited

FOREIGN PATENT DOCUMENTS 2038836 7/1980 United Kingdom .................... 424/85

OTHER PUBLICATIONS

W. Müller—Ruchholtz, et al., Transplantation Proceedings, vol. VIII pp. 537-541, 12/1976.

Reinherz, et al., The Journal of Immunology, vol. 123, No. 3, pp. 1312-1317, 9/1979.

Reisner, et al., Proc. Natl. Acad. Sci., vol. 77, No. 2, pp. 1164-1168, 2/1980.

Youle, et al., Proc. Natl. Acad. Sci., vol. 77, No. 9, pp. 5483-5486, 9/1980.

Raso, et al., J. of Immunology, vol. 125, pp. 2610-2616, 12/1980.

*Primary Examiner*—Richard J. Apley
*Assistant Examiner*—Greg Beaucage
*Attorney, Agent, or Firm*—Townsend & Townsend

[57] ABSTRACT

An improved transplantion therapy and method is provided which comprises specifically killing cells known to be problematic in the transplantion process. Novel compositions of the present invention are conjugates prepared by generating antibodies specific to surface receptors of the unwanted cells, preparing Fab or $F(ab')_2$ fragments from the antibodies, and coupling the fragments to A chains of lectins or other cytotoxic agents to render the conjugates thus formed strongly cytotoxic to the cells to which the antibody was directed. The conjugates are used in vitro to eliminate unwanted cells prior to bone marrow transplantation.

6 Claims, No Drawings

COMPOSITION AND METHOD FOR TRANSPLANTATION THERAPY

This is a division of application Ser. No. 276,579, filed June 23, 1981 now abandoned.

BACKGROUND OF THE INVENTION

This invention relates to transplantation therapies and, in particular, to novel compositions and methods for reducing the incidence of transplant rejection reactions and graft versus host disease.

Transplantation therapy is known whereby bone marrow or tissue, e.g., an organ, from a donor is infused into or grafted to a recipient. However, because of the frequency of life-threatening rejection reactions such therapies have only limited use. Typically such therapies are attempted only where the person's prognosis without transplantation therapy is exceedingly poor.

For example, bone marrow transplantation is currently limited to patients with severe, life-threatening diseases such as leukemia, aplastic anemia, and congenital immunodeficiency disease. For the success of the procedure, it is essential that the donor and recipient be matched by tissue typing tests including human leukocyte antigens (HLA) and mixed leukocyte culture (MLC). This matching requirement severely limits the number of patients who are even candidates for the procedure. The chances of finding an appropriate donor in the general population is exceedingly remote, although there has been an effort to tissue type large numbers of potential donors and provide matched tissues for recipients. More commonly the donor is a family member, but even then, the chances of finding a sibling who is matched with the patient is only one in four, and the chances that other family members will match the patient is considerably less.

The problem which occurs in bone marrow transplantation when donor and recipient are not matched, i.e. are allogenic, is that the transplanted cells of the donor recognize the recipient as foreign and attempt to reject the recipient's tissue, producing a condition termed graft versus host disease (GVHD). This results in skin rash, intestinal disease, and liver disease. These manifestations of GVHD may be severe and may lead to death. In patients with advanced GVHD, only 15% survive.

To perform a bone marrow transplant, one first locates a matched donor. It is necessary to render the recipient immunologically incompetent, i.e., to incapacitate the recipient's natural immunological system, so that he will not reject the donor marrow. This is done by the use of high dose total body radiation, chemotherapy, or a combination of the two. Marrow is obtained from the matched donor under general anesthesia in the operating room. This is done by inserting needles into the marrow cavity and aspiration of the marrow. Marrow is passed through screens to separate cells and then administered to the recipient intravenously or intraperitoneally.

A number of attempts have been made to get around the necessity of matching donor and recipient to avoid the development of GVHD. It is believed that GVHD is caused by the presence of mature thymic-derived lymphocytes (T cells) in the bone marrow preparation. It is believed that the more immature stem cells in the bone marrow are responsible for reconstitution of the recipient marrow and that they do not cause GVHD, probably because they are "educated" in the recipient and do not recognize the recipient as foreign.

Various approaches have been attempted in experimental animals whereby the mature T cels in the donor bone marrow are eliminated, and the recipient animal is reconstituted only with stem cells. Dicke et al. (1968) taught the separation of mature cells from stem cells using a discontinuous albumin gradient and demonstrated that these stem cells could reconstitute in irradiated mice without causing GVHD. Cantor (1972) teaches treatment of parental spleen or lymph node cells with anti-theta (antibody to T cells) and complement whereby GVH activity in the mouse is abolished.

Muller-Ruchholtz et al. (1976) disclose that by treating donor rat bone marrow cells in vitro with cytotoxic anti-lymphocyte sera (ALS) which had been made specific for mature T cells and pre-T cells by absorption, successful reconstitution of the cells in lethally irradiated rats across a strong histocompatibility barrier could be accomplished without GVHD.

The use of lectins peanut agglutinin (PNA) and soybean agglutinin (SBA) to fractionate murine bone marrow and spleen cells is known. Receptors for these lectins are present on the surface of immature thymocytes, and as such immature thymocytes can be isolated from bone marrow and spleen by agglutination with PNA and SBA. The immature or stem cells thus agglutinated were shown capable of reconstituting irradiated animals without production of GVHD.

Nevertheless, bone marrow transplantation is an experimental therapy which is only marginally successful at the present time. In only a minority of the patients is a matched donor available. Even with a matched donor, there are numerous complications. GVHD may develop, and survival is poor. The majority of patients lack a matched donor, and therefore bone marrow transplantation under the circumstances is not even a consideration. There have been only a few reports of successful reconstitution of bone marrow with tissue from an unmatched donor. The technique we propose will permit successful transplantation of donor marrow from unmatched donors without production of GVHD.

For transplantation of organs, such as kidney or heart, it is not essential that the donor and recipient be matched. In this circumstance, GVHD is not a problem, but an unmatched organ will be rejected by an immunocompetent recipient, i.e. a recipient capable of producing antibodies. To avoid rejection of the transplanted organ from an unmatched donor, to date it has been necessary to treat the recipient with immunosuppressive therapy. This usually consists of treatment of the recipient with azathioprine and a corticosteroid or cyclosporin. This type of immunosuppressive therapy produces broad suppression of all immune responses, including those to infections, and can lead to severe, life-threatening complications. Results of cadaveric renal transplantion vary, but at some centers, less than 40% of such transplants survive one year. Survival is less for heart transplants, and considerably less for transplants of other organs such as liver or lungs.

Among organ transplantion, that of kidneys is presently a useful therapeutic technique. Nonetheless, tissue typing is important, and results are less satisfactory if the donor and recipient are not well matched. Recipients of kidney transplants generally require administration of immunosuppressive agents which can produce serious complications, especially susceptibility to infectious diseases. Transplantation of other organs is highly experimental and not very successful because of the rejection process.

An object of the present invention are compositions and methods to improve organ transplantation and to permit transplantation of bone marrow from donors not necessarily matched to the recipient by tissue typing by specifically killing cells involved in the rejection process.

A still further object is to provide a method of bone marrow transplantation to provide a therapy for the following conditions:

a. Leukemia and other malignancies since it would permit use of extraordinarily large doses of radiation and/or chemotherapy.

b. Hematologic abnormalities such as sickle cell anemia, aplastic anemia, and others in which one of the elements of the blood is abnormal or in which the bone marrow is not functioning properly.

c. Congenital or acquired immunodeficient diseases such as severe combined immunodeficiency disease, chronic mucocutaneous candidiasis, the Wiskott-Aldrich Syndrome, and others in which the immune system is not functioning properly.

d. Nuclear holocaust, in which the bone marrow is destroyed and transplantation of marrow would be life-saving.

SUMMARY OF THE INVENTION

According to the present invention an improved transplantion therapy and method is provided which comprises specifically killing cells known to be problemmatic in the transplantion process. Novel compositions of the present invention are conjugates prepared by generating antibodies specific to surface receptors of the unwanted cells, preparing Fab or $F(ab')_2$ fragments from the antibodies, and coupling the whole antibody or its fragment to A chains of lectins or other cytotoxic agents to render the conjugates thus formed strongly cytotoxic to the cells to which the antibody was directed. According to this invention, the conjugates are used in vitro to eliminate unwanted cells prior to bone marrow transplantation.

DETAILED DESCRIPTION OF THE PREFERRED EMBODIMENT

Experimental Procedures

The cytotoxins or cytotoxic agents useful in the present invention are generally protein toxins or fragments thereof which upon entering a cell cause the death thereof. The term cytotoxin as used herein includes all such cytotoxic agents whether or not such agents are toxic or non-toxic in their naturally occurring state, i.e. whether or not in their natural state they are capable of cell entry. Known toxins useful in the present invention are those lectins which have a cytotoxic portion or fragment (termed "A" chain designating activity) and a cell attachment portion (termed "B chain") by which the toxin attaches to the cell surface and assists entry of the toxic portion into the cytoplasm. Many of these toxin fragments once inside the cell inactivate the protein synthesis mechanisms of the cell and thereby effect the death of the cell. For example, the A chain of ricin is known to inactivate the 60S ribosomal subunit of the cytoplasm upon cell entry. Illustrative of cytotoxins useful in the present invention ae the following lectins: ricin, abrin and modeccin.

To maintain the specificity necessary for selective cell killing, the whole toxins ricin, abrin, and modeccin cannot be employed as the B chains (binding portion) of these toxins nonspecifically bind cells. Therefore, for the purposes of this invention, the B chain would have to be removed or otherwise inactivated. Henceforth the term toxin or cytotoxin refers to the toxin having been altered either by removal of the B chain or by B chain inactivation.

Other cytotoxins useful in the present invention are lectins which are non-toxic as they naturally occur (due to the absence of any cell attachment and/or entry mechanism, i.e. "B chain" portion), but which nevertheless kill cells if introduced into the cytoplasm. Illustrative of "naturally non-toxic" cytotoxins include *Gelononium multiflorum, Phytolacca americana, Croton tigluim, Momordic chrentia,* wheat germ and mutant species of toxins specially cultivated for their absence of cell attachment or entry assisting portions, i.e., "B chains".

The antibodies useful in the present invention are specific for mature T-cells. For bone marrow transplantation a single antibody specific for all mature T cells or a group of antibodies each of which is specific for some mature T cells may be used. In particular, the antibodies must be able to distinguish mature T cells from virtually all other cells and especially from immature or stem T cells. It is the immature or stem T cells which will reconstitute the recipient. By reconstitute is meant take up residence, proliferate and repopulate the blood with the normal formed elements: red cells, white cells and platelets. Mature T cells, like all other cells, are distinguishable by their surface antigens. As such, antibodies useful in the present invention are those which are specific for one or more unique determinant sites on mature T cells. For purposes of this invention, the term antibody includes both the entire antibody and the portion or fragment thereof which determines specificity. Antibodies consist of a variable region (Fab) which includes the antigen-combining site and which has a different amino acid sequence for each specificity. Each antibody has two such antigen-combining sites (Fab). Each antibody also has one constant region (Fc) which has the same amino acid sequence and is responsible for other functions of the antibody, such as attachment to cells and complement fixation.

Antibodys may be treated with enzymes, such as papain or pepsin under controlled conditions to cleave the antibody into two or more fragments. For example, papain cleaves IgG antibody into three fragments—two F(ab) fragments or Fabs and one Fc fragment. Pepsin cleaves IgG into two fragments, a $F(ab')_2$ fragment and a Fc fragment. With reducing agents, $F(ab')_2$ fragments may be cleaved into two F(ab') units analagous to the Fabs derived from papain digestion. Under oxidizing conditions, two Fabs may be joined to form one $F(ab)_2$ fragment. For purposes of the present invention antibody is used to refer to whole antibodies or fragments thereof capable of identifying specific antigens, i.e. whole antibodies or fragments other than Fc fragments. In most instances a Fab or $F(ab')_2$ fragment will be used for coupling to the cytotoxin.

For tissue transplantation it is unnecessary and not desirable to kill all populations of mature T cells. Only those T cells having surface idiotypes or receptors which are capable of responding to tissue antigens of the donor need be killed or inactivated. By idiotype is meant the variable region of the antibody molecule containing a receptor specific for the antigen to which the antibody reacts. It is known that IgG antibodies and T lymphocytes with the same antigen-binding specificity have similar or identical idiotypes. This means that the way B cells (bone marrow derived lymphocytes) and T cells express their immune potential to histocompatibility, i.e. reject tissues, and other antigens is through representation on their surface of antigen-specific idiotypic receptors.

In the antibody-cytotoxin conjugates of the present invention, the intermolecular crosslinking of the antibody (or portion thereof) to the cytotoxin will be dependent upon which antibody or antibody fragment is used as well as the cytotoxin or toxin fragment employed. The conjugating agent may vary widely in chemical structure, but it will be covalently bound to the antibody portion and to the toxin portion with a biologically labile chemical bond contained between the two portions. The labile chemical bond may be at the point of attachment of the conjugating agent to one of the portions or be contained elsewhere in the conjugating agent. The biologically labile bond is simply a chemical connection which may be disconnected by the action of a natural or physiologically compatible agent to separate the binding portion (whole antibody or fragment) from the toxin portion. This disconnection may occur at any time after binding to the target cell so as to allow the toxin portion to be free (i.e. disconnected from the binding portion) inside the cell membrane. The conjugating agent is defined as anything which accomplishes connection of the two portions in a manner that satisfies the requirements stated previously. The conjugating agent can therefore vary from the coupling of the two portions directly in a suitably labile chemical connection in which the conjugating agent consists of no additional atoms, just those agents required to construct the conjugate, to a complex crosslinking agent that contains many atoms and functional groups. The methods commonly employed to connect two proteins utilize an alcohol, amine, thiol or carboxylic acid residue of one protein and an amine, thiol, alcohol or carboxylic acid residue of the other. Alternatively, the chemical linkage need not be labile. In some instances, the antibody-cytotoxin conjugate may be effectively used in its unseparated form.

Examples of direct linkages of the two portions without additional atoms are a disulfide formed between free thiols, an amide formed between an amine and a carboxylic acid, a thioester formed between a thiol and a carboxylic acid, an ester formed between an alcohol and a carboxylic acid, an azo or hydrazo bond between two amines, an hydroxyl amine formed between an amine and an alcohol, a sulfenate, sulfinate or sulfonate formed between an alcohol and a thiol, a peroxide formed between two alcohols or an anhydride formed between two carboxylic acids. The following is an illustration of how this is commonly done is in the formation of a disulfide by coupling two thiols:

reaction 1

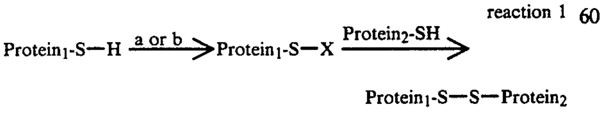

wherein a is $Na_2S_2O_3+Na_2S_4O_6$;

b is 5,5'dithiobis-(2-nitrobenzoic acid); and x is $SO_3^-$ when a is used and

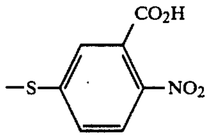
when b is used.

As depicted in Reaction 1 the sulfhydryl of one protein is activated (in this case either through the S-Sulfenate or thiophenyl derivative) for subsequent reaction with the sulfhydryl of the other protein to form the disulfide linked conjugate.

More diversity for connecting the two portions is available when the connection is made through the use of other atoms. The atom or atoms employed to connect the two pieces will be referred to as the crosslinking agent. As previously mentioned, the crosslinking agent will be covalently bound to both portions with a labile bond either at the point of connection or elsewhere in the crosslinking agent. Examples of labile bonds that could be employed in a crosslinking agent are disulfides, thioesters, Schiff's bases (imines), glycosidic linkages, phosphates, cleavable carbon-carbon bonds such as retroaldol condensations, Grob fragmentations and other like processes, and carbon-heteroatom cleavages such as those resulting from retroMichael additions and the like. Connection of the crosslinking agent to each portion may be via any of the previously mentioned chemical bonds as well as bond formation to carbon such as through alkylation, acylation or condensation to form carbon-carbon or carbon-heteroatom bonds.

The crosslinking agent may consist of any connection of atoms but will typically consist of 1 to 40 atoms comprising carbon atoms in any hybridization (sp, $sp^2$, $sp^3$) bound to other carbon, nitrogen, oxygen or sulfur atoms. The following are representative classes and examples of crosslinking agents that may be employed:

(a) Halo-imidates having the formula:

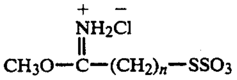

e.g. methyl 5-thiosulfatevalerimidate hydrochloride when n=4;

(b) Acyl-maleimides, such as m-maleimidobenzoyl-N-hydroxysuccinimide ester (MBS);

(c) Amino-disulfides such as cystamine dihydrochloride ($Cl^-H_3N^+CH_2CH_2S—S—CH_2CH_2N^+H_3Cl^-$);

(d) Acyl-disulfides having the formula:

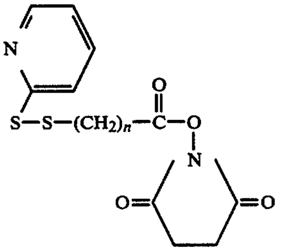

e.g. N-succinimidyl-3-(3-pyridyldithio)propionate (SPDP) when n=2

(e) Acyl-Sugars, such as

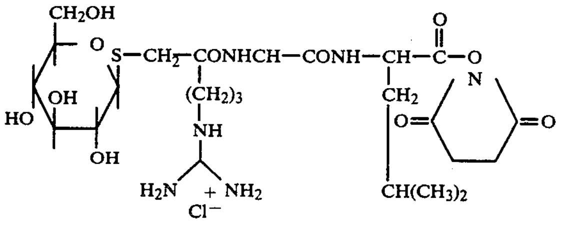

(2-(1-thio-β-D-glucopyranosyl)-ethanoyl-L-arginyl-L-leucine succinimide ester)

(f) Halo-maleimides, e.g. N-hydroxymethylmaleimidyl bromoacetate (g) Diimidates having the formula:

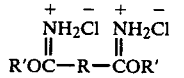

e.g., dimethyl suberimidate dihydrochloride when R' is $CH_3$ and R is $(CH_2)_6$ (h) bis Acyls having the formula:

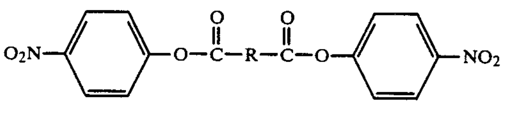

such as bis-p-nitrophenyl glutarate when $R=(CH_2)_3$ (i) bis-Isocynates, e.g. α,α'-diisocyanato-o-xylene;

(j) Dihalides, such as

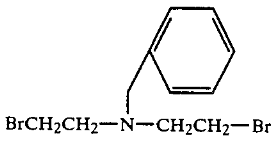

(bis(bromoethyl)benzylamine); and

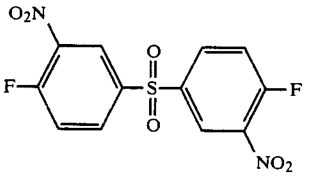

(bis(4-fluoro-3-nitrophenyl)sulfone);

(k) Dimaleimides, such as m-N,N'-dimaleimidobenzene;

(l) Azido-Acyls, e.g. N-Succinimidyl (4-azidophenyl)-1,3'-dithiopropionate (m) dialdehydes, e.g. gluteraldehyde Illustrative of the resulting crosslinked conjugates from the above functional group differentiated cross-linking agents are:

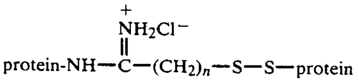

-continued

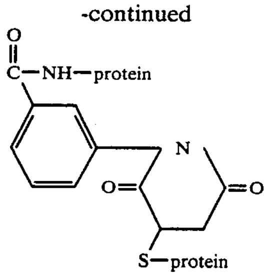

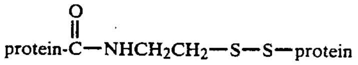

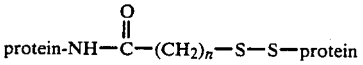

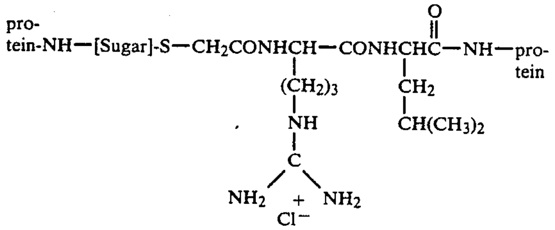

The cross-linking agents are all at least bifunctional reagents that react with first one protein and then the other. Typically each protein will be attached to the cross-linking agent through one of the following functional groups:

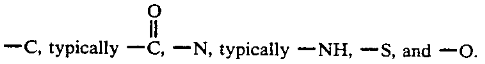

This allows for the necessary specificity required to maintain protein structure and function. The number of cross-linking sites vary from protein to protein, however, the number of crosslinks will normally be between 1 and 10. The only requirement is that the conjugate once formed is specific to the mature T cell or idiotype thereof and that upon attachment to the appropriate cell, entry of the cytotoxin into the cell take place.

The conjugates of the subject invention find use in vitro. When the conjugates are used in vitro to donor bone marrow having mixtures of cells and having different surface antigens, the subject invention provides for selective killing of the mature T cells as distinguished by their particular surface antigen.

The cytotoxic effect of the compounds of the subject invention can be achieved in nutrient media, or nutrient agar, with a cell confluent layer, or other convenient environment involving cell growth or cell maintenance. Normally, for transplantation therapy there will be a multiplicity of at least one conjugate per mature T cell, more usually at least about 10, and there may be 100 or more. Preferably, there will be a significant binding site excess of molecules of conjugates to numbers of cells. No particular manner of administration of the conjugates to the cells is required, so long as the administration provides contact between the conjugate and the cell.

The amount of the conjugate employed will vary widely, depending upon the number of idiotypic determinant containing cells to be killed, extent of the cell population, the resistance of the cell to the conjugate, the effectiveness of the conjugate, and the like. Although tissue typing of the donor and recipient may be useful in eliminating the number of such idiotypic determinants for which antibodies must be prepared, such typing is unnecessary to the practice of the present invention. The manner in which proteinaceous compositions may be administered to a host finds ample exemplification in the prior art and will not be expounded upon here.

The following examples are offered by way of illustration and not by way of limitation.

PREPARATION OF ANTI-T-CELL ANTIBODIES FOR USE IN BONE MARROW TRANSPLANT.

Specific antibodies useful in the present invention are obtained either by immunization of animals followed by appropriate absorption against tissue antigens other than those of the T cells or by generation of monoclonal antibodies using hybridoma technology. The latter will be described in detail, since it is an effective way of obtaining the appropriately specific antibody. The technique used is derived from that described by Kohler and Milstein (1975).

Human T cells are obtained by rosetting human lymphocytes with sheep red blood cells according to the method of Moretta et al. (1977). Human T cells will rosette while B cells will not. Peripheral blood is drawn from a normal human donor. Heparin is added. The mononuclear cell population is obtained by density gradient centrifugation on Ficoll-Hypaque. The mononuclear cells are washed and incubated with neuraminidase treated sheep red blood cells. The rosetted cells (T cells) are separated from the non-rosetted cells (B cells) by a second Ficoll-Hypaque centrifugation. The rosetted cell population is resuspended, and subjected to another Ficoll-Hypaque gradient. The rosetted cells are collected and treated with hypotonic ammonium chloride to lyse the red cells. The resulting lymphocyte (T cell) population is washed. This technique for isolating T cells is in common usage.

Mice are injected intraperitoneally with $2\times10^7$ of the purified T cells according to the method of Reinherz et al. (1979). Injections are repeated at 14 day intervals. Four days after the third immunization, the spleens are removed and a single cell suspension prepared. The cell line used for fusion is a mouse myeloma which is sensitive to hypoxanthine, aminopterin, and thymidine (HAT) containing medium. Several such lines are available. In addition, certain myeloma cell lines not required to be HAT-sensitive may also be used. Immunized splenocytes ($2\times10^7$) from the mouse are mixed with $2\times10^7$ myeloma cells, washed, and cultured in the presence of 35% polyethylene glycol (PEG) in 5% dimethyl sulfoxide (DMSO) in RPMI 1640. By fusion, the myeloma, i.e. cancerous B cells, which do not secrete antibody, are reprogrammed. Moreover, the fused myeloma or hybridoma cells, like healthy spleen cells, secrete antibody against whatever the spleen cell was immunized against. After fusion, the cells are washed twice, suspended at a concentration of $10^6$ cells per ml in RPMI 1640 with 15% fetal calf serum (FCS). The cells are placed in flat-bottom microtiter wells in 0.2 ml aliquots and cultured in HAT containing medium to select the hybrids. Unfused myeloma cells will die while fused myeloma cells will proliferate in the HAT medium.

To determine the presence of anti-mature T cell antibody in the supernatant, after three to four weeks of culture, the supernatants of wells containing hybridomas are tested for reactivity to human T cells and B cells using a radioimmunoassay or indirect immunofluorescence. Peripheral lymphocytes (T and B cell populations) are separated into populations which do (T) and do not (B) react with sheep red blood cells (Mendes et al., 1973). The separated cell populations are placed at 4° C. with the various hybridoma culture supernatants which contain antobody to mature T cells. Purified radiolabeled IgG sheep anti-mouse IgG is added. Cells are washed, and results analyzed using a scintillation counter. For immunofluorescence, the separated cell populations are placed at 4° C. with the various culture supernatants and fluorescenated IgG sheep anti-mouse IgG added. Results are analyzed using the fluorescence activated cell sorter (FACS manufactured by Becton-Dickinson) or cytofluorograph (manufactured by Ortho). Hybridoma clusters containing antibodies reacting with the T cells are selected. They are cloned by the limiting dilution method in the presence of feeder cells. Subsequently the clones are transferred to mice by injecting them into the peritoneal cavities of mice previously injected with pristane where the antibody secreting hybridoma cells grow.

An alternate way of selecting the appropriate clone following hybridization is through the use of the FACS or the Ortho cytofuorograph fitted with an attachment called a single cell deposition system. In such a case, the antigen is bound to a fluorescent bead and incubated with the hybridoma cells. The antigen carrying bead binds only to those cells producing the appropriate antibody. The cells are selected and viable cells which produce the appropriate antibody are deposited individually in single wells of the microtiter plate. They are subsequently cultured and tested as described hereinabove.

The reactivity of the monoclonal antibody is further characterized by measuring its reactivity with purified human T, B, null and macrophage populations and with T cell leukemia and lymphoid cell lines using the FACS. The function of the purified cell populations reactive with the antibody and nonreactive with the antibody is evaluated using standard mitogens including concanavalin A (Con A), phytohemagglutinin (PHA) and mixed leukocyte culture (MLC).

Human monoclonal antibodies may also be used. They may be produced and tested in a similar fashion through the use of huma-human hybridomas according to the method of Olsson and Kaplan (1980). In this case the myeloma is a human myeloma which is sensitive to HAT. The cells used for fusion are B cells from the peripheral blood, lymph nodes, or spleen, tonsils, etc. The donor of the immunized B cells is an individual having reactivity to T cells, such as a person who has received multiple blood transfusions. The technique for fusion, selection, and analysis of the clones is similar to that described above. Use of the human-human hybridoma has the advantage that the antibody produced is of human origin and thus is less likely to produce allergic reactions than is an antibody of mouse origin.

To generate monoclonal antibodies to the idiotypic determinants, it is first necessary to obtain a population of T lymphoblasts (mature T cells which have transformed upon exposure to foreign antigen into a blast state) from the potential organ transplant recipient which are responsive to the transplantation antigens of the donor. There are several ways this can be done. One is to generate the T lymphoblast population according to the method described by Andersson et al. (1977). This involves performing an MLC using the recipient's T cells cultured with irradiated lymphocytes from the donor. The donor's lymphocytes do not proliferate because they have been irradiated. Alternatively they may have been treated with agents such as mitomycin C. The recipient's lymphocytes bearing idiotypes for the donor antigens undergo blast transformation and proliferate.

It is possible that mitogenic factor generated in the MLC may cause nonspecific proliferation, i.e. that of other non-relevant lymphocytes. Therefore, it may be necessary to perform the cultures in the presence of antibodies to mitogenic factor to block this effect. After 5–6 days of culture, the cells are pooled and washed. They are resuspended and applied to a linear 15–30% Fetal Calf Serum (FCS) gradient. The gradient is harvested after five hours. The fractions containing blasts are determined, pooled, and washed.

Another way to generate the T lymphoblasts is through repeated exposure to the donor lympohcytes in long term MLC. The lymphocytes of the prospective recipient are cultured with an equal number of irradiated donor lymphocytes in the presence of 2-mercaptoethanol (2-ME). Every 20 days a subculture is set up and the cells restimulated by re-exposure to more irradiated donor lymphocytes. This is repeated four times. Five days after the final stimulation, the cells are harvested and washed.

A third and preferred means of generating T lymphoblasts is through cloning of the lymphocytes in soft agar in the presence of T cell growth factors (TCGF) according to the method disclosed by Sredni et al. (1981). Lymphocytes from the prospective recipient are cultured with irridated donor lympohcytes in a MLC. After 6 days of culture, the cells are harvested, washed, and placed in a soft agar system. The cultures are incubated for 3–6 days. Colonies are picked from the soft agar and cultured in flat-bottomed microtiter wells in the presence of irradiated lymphocytes from the donor and TCGF. The colonies are expanded and maintained by feeding every three days. Specific reactivity is tested by culturing the cells in the presence of irradiated donor lymphocytes and comparing results with reactivity to lymphocytes from an unrelated donor. Clones showing specific reactivity with the donor are selected and expanded. The T lymphoblasts are washed. Once the T lymphoblasts have been obtained, they are used to generate monoclonal antibodies in the mouse or human system, as described above. The resultant antibodies are tested for reactivity with the T lymphoblasts using a radioimmunoassay. The test culture supernatants containing anti-mature T antibodies are added to the target cells and incubated for one hour at 4° C. The cells are washed, and $^{125}I$ protein A added. The cell suspension is incubated for one hour at 4° C. after which the cells are again washed. Results are analyzed using a scintillation counter, and clones producing supernatants having reactivity with the target cells selected. The supernatants are further tested for their ability to specifically suppress mixed leukocytic reactivity between the prospective recipient's lymphocytes and irradiated donor lymphocytes in the presence of complement. Supernatants having this capacity are selected.

Once a repertoire of monoclonal antibodies is developed, it may not be necessary to develop a new one for each patient, but instead simply test the recipient and donor and select the antibody appropriate.

PREPARATION OF ANTIBODY $F(ab')_2$ FRAGMENT OR FAB $F(ab')_2$ fragments are obtained by standard technique (Stanworth and Turner, 1971). The monoclonal IgG is dissolved in Walpole's acetate buffer to give a 1–3 g % (grams/100 ml) solution. Crystalline pepsin is dissolved in a small amount of buffer. The pepsin is added to the IgG in a ration of one mg enzyme for every 100 mg IgG. The solution is incubated at 37° C. for 20–24 hours. Digestion is stopped by the addition of solid Tris salt to give a pH of 8.0. The product is applied to a Sephadex G-150 column and eluted with buffer at pH 7.4. Results are determined by reading density. The $F(ab')_2$ fragment elutes in the 5-S peak. These fractions are pooled, dialysed against distilled water and lyophilized. The reconsituted material is further fractionated on Sephadex G-200 for further purification. The $F(ab')_2$ fragments can be split into monovalent Fab' fragments by mild reduction with 0.01M mercaptoethanol followed by applying to an ion exchange column to remove the reducing agent.

PREPARATION OF THE A CHAIN OF ABRIN

For the preparation of A chains of abrin, decorticated abrus seeds are homogenized in 5% acetic acid as described by Olsnes and Pihl (1976). The extract is dialyzed against water and the precipitate removed. The supernatant is adjusted to 10 mM Tris-HCl (pH 7.7) and chromatographed on a DEAE cellulose (DE-52) column with the same buffer. The column is eluted with a NaCl gradient (from 30 to 180 mM). The most toxic fraction is applied to a Sepharose 4B column. The column is washed and the bound material eluted with 0.1 M-galactose to yield abrin. This is diluted with water. The pH is adjusted to 8.5. Galactose is added to a final concentration of 5%. The preparation is incubated for two hours at room temperature and at 4° C. overnight. The material is applied to a DEAF-cellulose (DE-52) column. The B chain passes through the column. The A-chain is bound and subsequently eluted with a 500 ml NaCl gradient (from 0 to 0.2M).

PREPARATION OF A CHAIN OF RICIN

For isolation of ricin, decorticated castor beans are homogenized in 0.14M NaCl and the pH adjusted to 4. This is dialyzed against distilled water and the precipitate removed. Na phosphate (pH 6.5) is added to a concentration of 5 mM and the solution applied to a carboxymethylcellulose column (CM-52). The bound material is eluted with a NaCl gradient (from 10 to 100 mM). The most toxic fraction is adjusted to pH 7.7 and applied to a Sepharose 4B column. The column is washed, and the bound ricin eluted with 0.1M galactose. To separate the constituent A and B chains, the ricin is treated exactly as described above for abrin. To purify the A-chain further, it is dialyzed against 5 mM Na phosphate (pH 6.5) and applied to a carboxymethylcellulose (CM-52) column. The pure A-chain is eluted from the column with a linear NaCl gradient (from 0 to 0.15M).

COUPLING OF A-CHAINS TO $F(ab')_2$ OR FAB'

The technique described by Raso and Griffin (1980) is used. The Fab' is reacted with Ellman's reagent (5,5'-dithio-bis-(2-nitrobenzoic acid) in 200 mM Na phosphate buffer, 3 mM ethylenediaminetetraacetic acid, pH 8.0. The mixture is incubated for two hours at 20° C. and excess reagent is removed by dialysis against buffer. Analysis at this point on a Sephadex G-100 column should show a single homogeneous peak corresponding to the Fab' fragment with its sulfhydryl group blocked by Ellman's reagent. 1.28 mg of purified A chain of abrin or ricin (see above) is added to 2 mg of the preparation in equimolar amounts at $2\times10^5$M final concentration. The results are analyzed by following the increase in absorbance of free Ellman's reagent as it is displaced by the A chain. When the reaction is near completion, the product is dialyzed against phosphate buffered saline (PBS). The Fab'-chain conjugate is purified on a G-100 column.

The efficacy of the conjugates as prepared above in eliminating mature T cells from the bone marrow population is assayed by incubating the bone marrow with various concentrations of the conjugates. The remaining population is washed and tested in MLC and for colony forming units (CFU-C) using the soft agar method for culturable myloid precursors, i.e. precursors of poly and mono-cytes as opposed to red cell and lymphoid precursors. (Pike and Robinson, 1970). Elimination of MLC reactivity and maintenance of a high proportion of colony forming cells in the remaining population is observed.

Similarly prepared conjugates for in vivo use in kidney and other organ transplantation are tested for efficacy by assessing its ability to eliminate MLC reactivity in cultures of the prospective recipient's lymphocytes with irradiated lymphocytes of the prospective donor.

IN VITRO ADMINISTRATION OF CONJUGATES FOR BONE MARROW TRANSPLANT

For bone marrow transplantation, marrow is obtained from the selected donor by standard techniques. Under general anesthesia in the operating room, marrow is aspirated from the marrow cavities into syringes containing sterile, preservative-free heparin. The marrow is passed through a sterile stainless steel screen to remove particles and produce a single cell suspension. The resulting cell population is incubated with the A chain conjugate containing Fab' or $F(ab')_2$ fragments of monoclonal antibody for mature T cells. The cells are washed and subjected to Ficoll-Hypaque gradient centrifugation to eliminate dead cells. The cells are washed again and infused into the recipient, who has been rendered immunoincompetent by irradiation and/or chemotherapy.

Although the foregoing invention has been described in some detail by way of illustration and example for purposes of clarity of understanding, it will be obvious that certain changes and modifications may be practiced within the scope of the invention, as limited only by the scope of the appended claims.

What is claimed is:

1. A method of transplanting bone marrow from a donor to host comprising the steps of:

(a) removing a sample of bone marrow from the donor;

(b) incubating said sample with a composition useful in transplantation therapy which is a conjugate of a monospecific anti-mature T-cell antibody and a cytotoxin for mature T-cell to kill any mature T-cell present in said sample; and (c) introducing said bone marrow sample into the host.

2. In the method of transplanting bone marrow from a donor to an immunologically incompetent host wherein a bone marrow sample comprising mature and immature T-cells is removed from the donor and injected into said host, the improvement comprising killing the mature T-cells of said sample prior to injecting said sample into said host by incubating said sample with an anti-mature T-cell-toxin conjugate prepared by the steps of:

(a) preparing a monospecific antibody to mature T-cells; and (b) conjugating said antibody to a cytotoxin for mature T-cells.

3. A method according to claim 2 wherein said monospecific antibody to mature T-cells is a monoclonal antibody and is prepared by fusing a cell which produces anti-mature T-cell antibody with a myeloma cell.

4. A method according to claim 2 wherein said cytotoxin is the A chain of a toxin selected from the group consisting of lectins and diphtheria.

5. A method in accordance with claim 2 wherein the antibody of said conjugate is an antibody fragment selected from the group consisting of Fab, Fab', $Fab_2$ and $F(ab')_2$ fragments.

6. A method according to claim 5 wherein said Fab fragment is obtained by enzymatic cleavage of said anti-mature T-cell antibody.

* * * * *